United States Patent
Moore et al.

(10) Patent No.: US 9,517,308 B2
(45) Date of Patent: Dec. 13, 2016

(54) DOSE SETTING MECHANISM AND METHOD OF SETTING A DOSE

(75) Inventors: David Moore, Leicestershire (GB); Joseph Butler, Warwickshire (GB); David Martin Leak, Lake Hopatcong, NJ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 913 days.

(21) Appl. No.: 13/878,762

(22) PCT Filed: Oct. 11, 2011

(86) PCT No.: PCT/EP2011/067676
§ 371 (c)(1),
(2), (4) Date: Apr. 11, 2013

(87) PCT Pub. No.: WO2012/049139
PCT Pub. Date: Apr. 19, 2012

(65) Prior Publication Data
US 2013/0296802 A1    Nov. 7, 2013

Related U.S. Application Data

(60) Provisional application No. 61/392,745, filed on Oct. 13, 2010.

(30) Foreign Application Priority Data

May 31, 2011    (EP) .................... 11168188

(51) Int. Cl.
*A61M 5/315*    (2006.01)
*A61M 5/24*    (2006.01)

(52) U.S. Cl.
CPC ........... *A61M 5/31535* (2013.01); *A61M 5/24* (2013.01); *A61M 5/31525* (2013.01); *A61M 5/31551* (2013.01); *A61M 5/31585* (2013.01)

(58) Field of Classification Search
CPC .................... A61M 5/31533; A61M 5/31535; A61M 5/3155; A61M 5/31551; A61M 5/31558; A61M 5/31525; A61M 5/31528; A61M 5/31536; A61M 5/31548; A61M 5/31563; A61M 2005/3154; A61M 2005/2093
See application file for complete search history.

(56) References Cited

U.S. PATENT DOCUMENTS 5,827,232 A * 10/1998 Chanoch ........... A61M 5/31551
                                                          604/208
7,377,913 B2 * 5/2008 Gurtner ............. A61M 5/31553
                                                          604/211
(Continued)

FOREIGN PATENT DOCUMENTS

| CN | 101107032 | 1/2008 |
| CN | 101262899 | 9/2008 |

(Continued)

OTHER PUBLICATIONS

English Translation of Notice of Reasons for Rejection issued in Japanese Patent Application No. 2013-533169 dated Oct. 6, 2015.
(Continued)

*Primary Examiner* — Laura Bouchelle
*Assistant Examiner* — Justin L Zamory
(74) *Attorney, Agent, or Firm* — McDonnell Boehnen Hulbert & Berghoff LLP

(57) ABSTRACT

A dose setting mechanism comprises a drug delivery device housing and a dual state track provided within the housing that is axially and rotationally fixed with respect to the housing. A dose dial component is positioned in the housing and rotatable during dose setting and dose delivery. A clutch is rotatable during dose setting and non-rotatable during (Continued)

dose delivery. A clutch plate is rotationally fixed relative to the housing; and a clutch blocker is in threaded engagement with the clutch plate and has a radial key engaged with the dual state track. The mechanism may comprise a biasing member positioned between the clutch blocker and clutch plate.

14 Claims, 5 Drawing Sheets

(56) References Cited

U.S. PATENT DOCUMENTS

| | | | |
|---|---|---|---|
| 7,811,263 B2 * | 10/2010 | Burren | A61M 5/24 604/207 |
| 7,955,303 B2 | 6/2011 | Burren et al. | |
| 9,011,391 B2 | 4/2015 | Veasey et al. | |
| 2004/0030292 A1 | 2/2004 | Gurtner | |
| 2004/0267207 A1 * | 12/2004 | Veasey | A61M 5/24 604/208 |
| 2009/0012479 A1 | 1/2009 | Moller et al. | |

FOREIGN PATENT DOCUMENTS

| | | |
|---|---|---|
| EP | 1074273 A1 | 2/2001 |
| EP | 2351591 A1 | 8/2011 |
| JP | 2006519074 A | 8/2006 |
| JP | 2009518056 A | 5/2009 |
| WO | 02064199 A1 | 8/2002 |
| WO | 2004078239 A1 | 9/2004 |
| WO | 2004078241 A1 | 9/2004 |
| WO | 2006061395 A2 | 6/2006 |
| WO | 2008087386 A1 | 7/2008 |
| WO | 2009097934 A1 | 8/2009 |

OTHER PUBLICATIONS

Chinese Office Action for CN App. No. 201180059706.X, dated Aug. 6, 2014.

Form PCT/IPEA/416, Notification of Transmittal of the International Preliminary Report on Patentability.

* cited by examiner

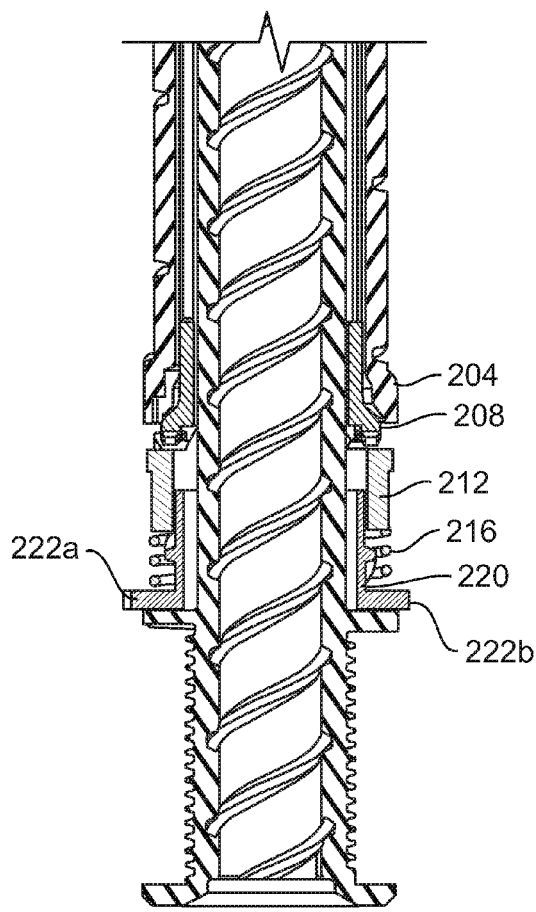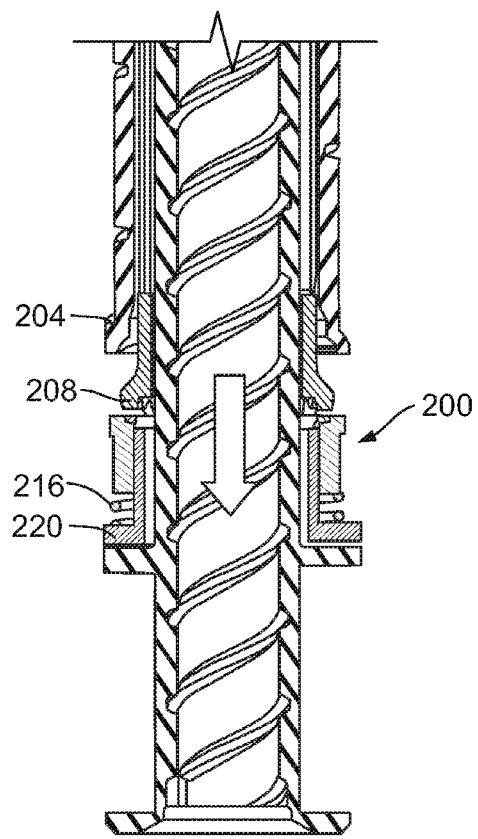
FIG. 7
FIG. 8

DOSE SETTING MECHANISM AND METHOD OF SETTING A DOSE

CROSS REFERENCE TO RELATED APPLICATIONS

The present application is a U.S. National Phase Application pursuant to 35 U.S.C. §371 of International Application No. PCT/EP2011/067676 filed Oct. 11, 2011, which claims priority to U.S. Provisional Patent Application No. 61/392,745 filed Oct. 13, 2010 and European Patent Application No. 11168188.8 filed May 31, 2011. The entire disclosure contents of these applications are herewith incorporated by reference into the present application.

FIELD OF INVENTION

The present patent application is generally directed to dose setting mechanisms for drug delivery devices that control minimum and/or maximum possible dose settings and to a method of setting and delivering a dose, preferably with such a drug delivery device that controls minimum and/or maximum possible dose settings. More particularly, the present patent application is generally directed to drug delivery devices, such as pen type drug delivery devices where therapy demands that a patient receive at least a certain minimum dose and not exceed a certain maximum dose of a particular medicament. Such devices provide for self-administration of medicinal product from a multi-dose cartridge and contain dose limiting mechanisms for setting minimum and/or maximum doses. The present application may find application in both disposable and reusable type drug delivery devices. However, aspects of the invention may be equally applicable in other scenarios as well.

BACKGROUND

Self administered injectable medicaments are often delivered using a variable-dose injection device. Such a device is known from WO 2004/078239 A1. Prior to the injection the user selects the dose that they require according to their prescribed dose and/or their current or expected future physical condition. A typical example would be an insulin delivery device for diabetics where a patient's dose is determined according to their prescribed dose and their expected food intake and activity level. Typically such devices allow the user to select any dose from 1 unit up to the maximum unit dose that the device can deliver, typically 60 units or 80 units for a manual device, such as a pen-type or syringe injection device.

Pen type drug delivery devices have been designed and developed to perform regular injections by persons without formal medical training. This is increasingly common among patients having diabetes where self-treatment enables such patients to conduct effective management of their disease. Because the patient, and not the health care worker, may be using such a drug delivery device, one requirement is that the device should be robust in construction. The drug delivery device must also be easy to use both in terms of the drug delivery device manipulation and understanding of the device's operation. This is especially true for diabetics who are required to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

In addition to insulin, other medicaments require a minimum dose to be delivered before they are therapeutically effective. A variable-dose device that allows the patient to deliver doses below the therapeutically effective minimum dose creates the possibility that the user may deliver the ineffective doses either by an error of dose calculation or by mistakenly selecting the incorrect dose. Likewise, some medicaments require that a maximum dose is not to be exceeded. This may be for safety reasons such as increased risk or severity of side-effects or excessive or unwanted actions of the medicament. Current variable-dose delivery devices typically have a maximum dose that is limited by the maximum dose that the delivery mechanism can provide, however, this does not necessarily relate to the maximum advised or prescribed dose of the medicament.

From WO 02/064199 A1 with a device for administration of an adjustable dose of an injectable product with an adjustment lock for the set dose is known that prevents inadvertent change of the set dosage. While being connected to a housing, dosing and actuating means perform the functions of the dose setting and the operation of a conveyor. In order to lock the dose set, a plug-in body is attached to the injection device's body, said body comprising a first and second plug-in body portion. The first plug-in body portion axially fixes the plug-in body to the injection device, while the second performs the function of shielding the dosing element against adjusting movements by the user, thereby preventing unintended change of the set dose.

EP 2 351 591 A1 is directed at a device with an end-stop mechanism that prevents dialing once a final dose is reached, said mechanism including a stop feature located at a rotation member, a drive member rotationally coupled to a piston rod by means of a longitudinal guide rib/notch-connection and further coupled to the rotation member by means of a uni-directional clutch mechanism. The piston rod comprises a blocking member interacting with the stop feature on the rotation member. With each injection process, blocking member and stop feature advance towards each other. Once blocking member and stop feature abut, rotation of the stop feature and the rotation member is prevented.

SUMMARY

It is an object of the invention to provide a device that reduces or eliminates the risk that a user of an injection device will set and administer a dose either below a preselected minimum effective dose of a particular medicament.

This object is solved with a dose setting mechanism as defined in claim 1. The present invention has at least two applications. First, is the delivery of a single active medicament which must be a variable dose within a defined dose window, i.e. the dose must be more than a certain minimum dose and must not exceed a certain maximum dose. The second application relates to the delivery of a combined formulation of active medicaments where at least one of the medicaments is preferably delivered as a variable dose and at least one other medicament is preferably delivered as a fixed dose, and where this fixed dose can safely be allowed to vary within a defined dose window, for example by ±10% of the nominal fixed dose.

The minimum and/or maximum dose limited delivery device in accordance with our disclosure could be used for a medicament that requires a minimum dose to be delivered before it becomes therapeutically effective, but where a degree of dose adjustment may be required. This dose adjustment may be required for a number of reasons, including tailoring a dose to a patient's body weight or the severity of their medical condition. The minimum and maximum dose limited device (min/max device) may also be used instead of a fully variable (i.e., 0 to max dose) device in order to reduce the possibility for dosing errors by the patient. Using the min/max device rather than a variable dose pen reduces the risk that a patient might accidentally deliver a dose outside the defined dose window, i.e., either too high or too low.

One example of the utility of the min/max device is where a parent could give the min/max delivery device to a child for the child to self-administer and the parent would know that the minimum and maximum levels of the min/max device limited the possible severity of any overdose or under dose. Another example of where such a device might be applicable is for patients who take long acting insulin. Typically a variable dose pen is required when a patient is "titrating" their dose to reach their target blood glucose level. However, once the target blood glucose level has been achieved the dose of long acting insulin typically remains more or less constant over relatively long periods of time. During this period, where their insulin dose is either constant or changes by only a few units on a day-to-day basis, the patient's long acting insulin needs could be effectively met by the minimum and maximum dose limited delivery device.

Table 1 (provided below) shows an example family of delivery devices, "Pen 1" through "Pen 4", which could be used in place of a single 1-80 unit variable dose device. Each of the Pens 1-4 are designed and manufactured around the same basic mechanism, but each pen contains either additional or alternative components which are used to set a different minimum and maximum dose. Patients would be prescribed a particular Pen according to their stable long acting insulin dose. For example, according to Table 1 a patient prescribed 30 units per day of long acting insulin would be prescribed Pen 2, which has a minimum dose of 18 units and a maximum dose of 42 units, respectively. Any number of mechanical components can be used in such a pen design to ensure these predetermined min/max doses, including axial and/or rotational stops, detents, clutches, compressible fingers, or the like components. In an example, a clutch plate may be threaded engagement with a clutch blocker to prevent axial movement of a clutch unless a dose greater than a predefined minimum dose has been selected.

The insulin dose of diabetic patients may change gradually over time. Therefore there may be a small amount of dose range overlap between Pens to allow for a smooth transition between Pens as the dose increases. For example, according to Table 1 a patient prescribed 40 units per day of long acting insulin would be given Pen 2 if they expected their dose to decrease over time or Pen 3 if they expected their dose to increase over time. The number of pens in the "family" and the selected dose ranges shown in Table 1 are illustrative only. By using the min/max device of the present invention a potential mistake when selecting the dose is limited to within the pen's operating window. Dialing a dose above or delivering a dose below the pen's dose range would not be possible and this would alert the patient to their error.

The min/max device may also be applicable for the delivery of other medicines, particularly where there is a risk of confusion with similar devices that may lead to dose errors or drug/device mix-ups. One such example would be rapid acting insulin and long acting insulin. Both of these insulins are measured in "units" however the same number of units of each insulin type will have a very different effect and a patient will be prescribed different doses of each drug to be taken at different times throughout the day. A mix up of long acting and rapid acting insulin can cause hypoglycemia and is potentially fatal. Both types of insulin may be delivered by injection pen devices. Patients perform their injections on such a routine basis that an "automatic pilot" effect can occur where patients have been known to mix up their insulin pens, even though the pens are of different design, color, shape and carry different labels.

The presently proposed min/max device may help to prevent this mix up occurring. For example, assume both rapid acting and long acting insulins were each provided with a family of min/max devices according to Table 1. A patient is prescribed 50 units per day of long acting insulin (which would require long acting Pen 3) and 15 units of rapid acting insulin with meals (which would require Pen 1). The most dangerous mix up could occur if the patient mistakenly delivered 50 units of rapid acting insulin rather than long acting insulin. If the patient attempted to do this with the min/max devices then the patient would pick up the rapid insulin device (Pen 1) and find that they could not dial beyond 22 units. This should alert them to the fact that this is not the correct insulin pen, and therefore the incorrect insulin type, and prevent the incorrect insulin being delivered.

The min/max concepts may be applied equally to both disposable devices and reusable devices.

Certain medicines also require the user to perform a "priming" dose to confirm the correct operation of the delivery device and needle. This is usually accomplished by delivering an "air-shot" of 2 units and then checking that the medicine can be seen coming out of the needle. The min/max concept shown in Table 1 would not permit this. If priming functionality is required a second permissible "dose window", for example ranging from 1-2 units, may also be implemented within each pen mechanism. An example of how this could be applied is shown in Table 2. Although both Tables 1 and 2 show only even numbers of units this is done only for clarity and the device may be configured to deliver odd and even units or potential ½ units. In one exemplary dose setting mechanism, a clutch plate may be in threaded engagement with a clutch blocker to prevent axial movement of a clutch unless a dose greater than a predefined minimum dose has been selected. However, in one arrangement, the dose setting mechanism allows axially movement of the clutch if a priming dose has been selected. Such a priming dose may comprise a dose of more than 1 unit and less than 4 units.

As mentioned, the presently disclosed devices may also be useful in therapies where the delivery of a combined formulation of active medicaments is needed, where at least one of the medicaments is preferably delivered as a variable dose and at least one other medicament is preferably delivered as a fixed dose. If a patient requires a combination of medicines then there is an advantage if those medicines can be provided as a single formulation (i.e. both drugs are mixed together in predefined proportions and supplied in one primary pack) for delivery by a single injection device in one injection through a single needle. However, if one of the drugs requires the delivery of a user-selectable variable dose and the second drug requires a dose above a minimum dose to be therapeutically effective and must not exceed a given maximum dose, then it is beneficial for the drug delivery device to be configured such that it is prevented from delivering doses that are outside of this range.

For example, a patient may be prescribed a combination therapy of long acting insulin (typically delivered in variable dose devices) and GLP-1 (typically delivered as a fixed dose). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of investigation as a potential treatment of diabetes mellitus. In order to avoid the patient having to perform two injections the two medicines are pre-mixed into a single formulation. Since both medicaments are pre-mixed in a fixed ratio it is not possible to vary the long acting insulin dose without also varying the GLP-1 dose. However, it may be acceptable for the GLP-1 dose to vary within a given tolerance, for example ±10%, around a fixed nominal dose. It is therefore possible, using a family of minimax limited devices to provide a family of pre-mix devices which between them will allow delivery of a variable long acting insulin dose and a GLP-1 dose that always falls within ±10% of a given "fixed" dose.

Table 3, for example, shows a family of 6 min/max pen-type injection devices that allow the delivery of any long acting insulin dose from 22-76 units along with a GLP-1 dose that is "fixed" to 20 mg±10%. Each pen within the family would have different minimum and maximum dose thresholds and would be provided with a primary pack or cartridge of medicament filled with the appropriate mix ratio of the two medicines. The family of pen devices could be provided as disposable mechanical devices, prefilled with the appropriate mix ratio cartridge of medicament. Alternatively, the family of devices could be provided as reusable mechanical devices. In the latter case, the devices would be preferably dedicated to a particular mix ratio cartridge, i.e. only the correct mix ratio cartridge can be loaded into each pen family member.

A third alternative is to provide the "family" of pen devices via a single electronic device that can be programmed with the minimum and maximum dose functionality. Preferably, the min/max electronic device would be loaded with a coded cartridge that would automatically upon being loaded into the device communicate to the device what the required minimum and maximum thresholds should be for that particular cartridge and mix ratio.

One specific means of achieving a minimum settable dose on a variable dose, drug delivery device, such as a pen-type device, is to include a mechanism that prevents dosing of the device until a predetermined minimum dose has been reached. A maximum dose mechanism can also be used with a minimum dose mechanism.

The overall design and function of the drug delivery device according to the present invention is preferably mainly identical to that of the device disclosed in WO 2004/078239 A1 which comprises a housing for receiving a dose setting mechanism, a cartridge, a dose dial sleeve (dose count number sleeve) with an attached dose dial grip, a clicker, a drive sleeve, a clutch for coupling and decoupling the dose dial sleeve and the drive sleeve, a rotatable piston rod and a button which is pressed for injecting a set dose. The full description of the pen-type injection devices disclosed in WO 2004/078239 A1 is incorporated herein by reference.

In an initial position or state, the clutch means rotationally couples the dose dial sleeve (number sleeve) to the drive sleeve. To dial a dose a user rotates the dose dial grip of said device. With the clicker and clutch means engaged, the drive sleeve, the clicker, the clutch means and the dose dial sleeve rotate with the dose dial grip relative to the housing and relative to the piston rod. Audible and tactile feedback of the dose being dialed is provided by the clicker and the clutch means. Torque is transmitted through saw teeth between the clicker and the clutch means.

A helical groove on the dose dial sleeve and a helical groove in the drive sleeve have the same lead. This allows the dose dial sleeve to extend from the housing and the drive sleeve to climb the piston rod at the same rate. At the limit of travel, a radial stop on the dose dial sleeve engages a stop provided on the housing to prevent further movement. Rotation of the piston rod is prevented due to the opposing directions of overhauled and driven threads on the piston rod.

Should a user inadvertently dial beyond the desired dosage, the pen-type injector allows the dosage to be dialed down without dispense of medicinal product from the cartridge. The dose dial grip is counter rotated. This causes the system to act in reverse. The torque transmitted through the clutch means causes the saw teeth to ride over one another to create the clicks corresponding to dialed dose reduction. Preferably the saw teeth are so disposed that the circumferential extent of each saw tooth corresponds to a unit dose.

When the desired dose has been dialed, the user may then dispense this dose by depressing the button. This displaces the clutch means axially with respect to the dose dial sleeve causing dog teeth of the clutch means to disengage. Thus, the clutch means rotationally de-couples the dose dial sleeve (number sleeve) from the drive sleeve at the beginning of an injection step. However the clutch means remains keyed in rotation to the drive sleeve. The dose dial sleeve and associated dose dial grip are now free to rotate relative to the drive sleeve. The axial movement deforms a flexible part of the clicker to ensure the saw teeth cannot be overhauled during dispense. This prevents the drive sleeve from rotating with respect to the housing though it is still free to move axially with respect thereto. This deformation is subsequently used to urge the clicker and the clutch back along the drive sleeve to restore the connection between the clutch and the dose dial sleeve when pressure is removed from the button. The longitudinal axial movement of the drive sleeve causes the threaded piston rod to rotate through a threaded opening in a housing insert, thereby to advance the piston in the cartridge.

In other words, the drive sleeve moves longitudinally, i.e. only in the axial direction, during an injection. Because the drive sleeve and the piston rod are engaged via corresponding threads on the outer surface of the piston rod and an internal face of the drive sleeve, the longitudinal movement of the drive sleeve causes the piston rod to rotate. The housing insert with the threaded opening which is engaged with the piston rod via corresponding threads is fixed within the housing, i.e. prevented from rotation. Thus, the rotating piston rod is screwed through the threaded opening in the housing insert, i.e. the piston rod performs a combined rotational and longitudinal movement along a helical path defined by the corresponding threads of the threaded opening and the piston rod.

Once the dialed dose has been dispensed, the dose dial sleeve is prevented from further rotation by contact of a plurality of members extending from the dose dial grip with a corresponding plurality of stops formed in the housing, thus determining a zero dose position.

In contrast to the disclosure of WO 2004/078239 A1, the minimum dose limiting function as disclosed herein may be achieved by means of a clutch plate and a clutch blocker. For example, a dose setting mechanism for a drug delivery device may comprise a drug delivery device housing and a dual state track provided within the housing that is axially and rotationally fixed with respect to the housing. A dose dial component is positioned at least partly in the housing and rotatable during dose setting and dose delivery. A clutch is rotatable during dose setting and non-rotatable during dose delivery. A clutch plate is rotationally fixed relative to the housing; and a clutch blocker is in threaded engagement with the clutch plate and having a radial key engaged with the dual state track. The clutch blocker acts to block the release of the clutch until the minimum allowable dose is dialed. The geometry of the dual state track controls the release of the clutch blocker from the clutch thereby controlling the minimum allowable dose. The mechanism may comprise a biasing member positioned between the clutch blocker and clutch plate. In an example of our min/max device, the dose count numbers (which are according to a specific embodiment shown on the dose dial component) below the minimum dose may be colored a different color such as red to differentiate that the dose dialed is less than the normal minimum dose.

The present invention is based on the idea that the dose dispensing operation of a device, like the device described in WO 2004/078239 A1, requires the steps of pushing via a button the clutch member in the distal direction, thus de-coupling the dose dial component from the drive sleeve. This de-coupling step is necessary to allow the dose dial component to be rotated back into the housing along a helical path while the clutch member and the drive sleeve which is rotationally fixed to the clutch are allowed to move axially in the distal direction. Thus, if this de-coupling of the clutch is prevented, the dose dispensing operation is prevented, too.

To achieve this, a spring between the clutch blocker and the clutch plate is expanded in an initial position, i.e. the clutch plate is located at the proximal end of the clutch blocker. In addition, the clutch sleeve abuts the clutch plate with teeth engaging the clutch plate keying feature. Thus, as the clutch blocker and the clutch plate are in threaded engagement any axial movement of the clutch plate (induced by a distal movement of the clutch sleeve during operation) relative to the clutch blocker in the distal direction would also require a relative rotational movement between the clutch blocker and the clutch plate along the helical path of the outer thread. However, if the clutch blocker and the clutch plate, are held unrotatably within the housing, preferably via splines, the clutch is prevented from moving in a distal direction by the clutch blocker. In this initial position, the dual state path constrains the clutch blocker radial key to move axially without rotation up to a minimum dose limit.

According to a preferred embodiment, the dual state track, the clutch plate and the clutch blocker are configured to prevent a relative axial and/or a relative rotational movement between the clutch plate and the clutch blocker if a set dose is less than a minimum predetermined dose. Thus, the dose dispensing operation of the device is prevented as long as the set dose is less than the minimum predetermined dose.

Those skilled in the art will understand that different designs and configurations of the component parts are possible to achieve this function. Preferably, the clutch plate is a sleeve-like or ring-like component. The clutch plate may comprise means for rotationally coupling the clutch plate to the clutch member, like at least one tooth or detent meshing with corresponding teeth of the clutch member. Further, the clutch blocker may be configured as a sleeve-like component, too. Preferably, the clutch blocker is at least partly surrounded by the clutch plate, i.e. the clutch blocker may be a sleeve with an outer thread and the clutch plate may be a nut-like component.

These as well as other advantages of various aspects of our proposed drug delivery device will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 7 illustrates a cross sectional view of an initial position of the dose setting mechanism illustrated in FIG. 2 before a minimum dose has been selected; and FIG. 8 illustrates a cross sectional view of a second position of the dose setting mechanism after a minimum dose has been selected and the selected dose is being administered.

DETAILED DESCRIPTION

Figure 1:
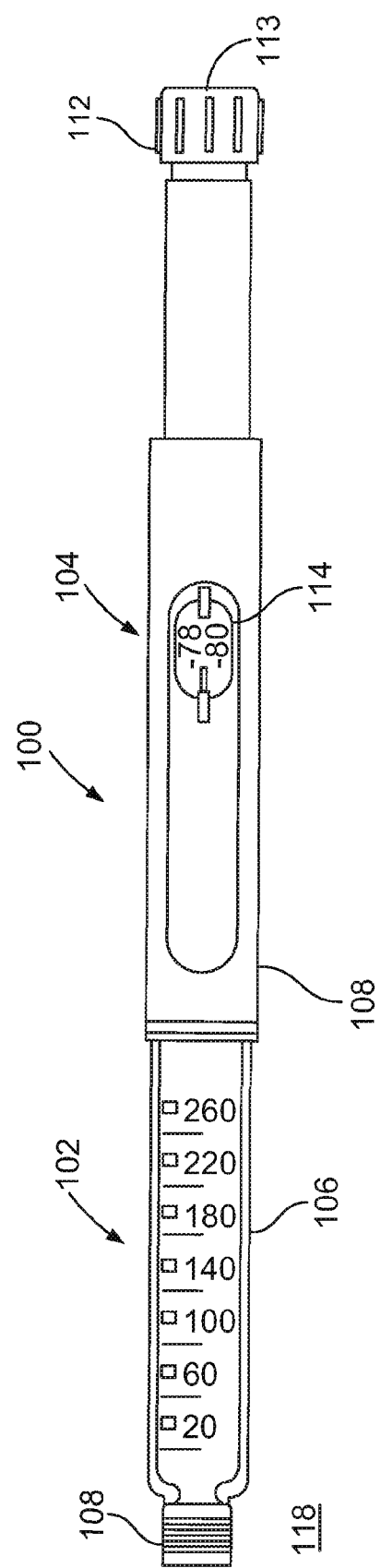
FIG. 1 illustrates an exemplary design of a pen-type drug delivery device.

Referring to FIG. 1, there is shown a drug delivery device 100 in accordance with an exemplary pen-type design arrangement. The drug delivery device 100 comprises a housing having a first cartridge retaining part 102 and a dose setting mechanism 104. As will be explained with respect to FIG. 2, the dose setting mechanism 104 may comprise multiple component parts such as a piston rod, a dose dial sleeve, a drive sleeve, and a clutch. These various component parts may be assembled within a dose setting mechanism outer housing or shell 108. The overall structure and functionality of the pen-type injection device 100, specifically the interaction of a drive sleeve, a clutch means, a dose dial sleeve, a housing and a piston rod during both dose setting and dose delivery is described in detail in WO 2004/078239 A1.

The drug delivery device 100 may be a resettable drug delivery device (i.e., a reusable device) or alternatively a non-resettable drug delivery device (i.e., a non-reusable device). A first end of the cartridge retaining part 102 and a second end of the dose setting mechanism 104 are secured together by connecting features. For non-resettable devices, these connecting features would be permanent and non-reversible. For resettable devices, these connecting features would be releasable.

In this illustrated arrangement, the cartridge retaining part 102 is secured within the second end of the dose setting mechanism 104. A removable cap (not shown) is releasably retained over a second end or distal end of a cartridge retaining part or cartridge housing. The dose setting mechanism 104 comprises a dose dial grip 112 and a window or lens 114. A dose scale arrangement, such as a dose scale arrangement provided along an outer surface of the dose dial sleeve, may be viewable through the window or lens 114. To set a dose of medication contained within the drug delivery device 100, the dose dial grip 112 can be rotated such that a dialed dose will become viewable in the window or lens 114 by way of the dose scale arrangement. The selected dose may be injected by pressing on a dose button 113.

As will be described in greater detail below, in one alternative dose setting mechanism arrangement, a visual indication may be provided along an outer surface of the dose dial component. Such an indication may be viewable by a user through the lens 114 if less than minimal dose has been dialed. For example, the color red may be seen through the window if a dose less than a predetermined minimum dose has been set and therefore the device would not be enabled to inject this set dose. In such an exemplary arrangement, once a dose greater than the minimum dose has been set, a numerical dose setting scale may be viewed within the lens, thereby providing notice to the user that an injectable dose (i.e., a dose greater than the predetermined minimum dose) has now been set.

FIG. 1 illustrates the medical delivery device 100 with the cover cap removed from a distal end 118 of the medical delivery device 100. This removal exposes the cartridge housing 106. Preferably, a cartridge (not shown) from which a number of doses of a medicinal product may be dispensed, is provided in the cartridge housing 106. Preferably, the cartridge contains a type of medicament that can be administered relatively often, such as once or more times a day. One such medicament is either long acting or short acting insulin or an insulin analog; however, any medicament or combination of medicaments is possible. The cartridge comprises a bung or stopper that is retained near a second end or a proximal end of the cartridge. The dose setting mechanism 104 of the drug delivery device 100 further comprises a spindle or piston rod that is driven in the distal direction by the drive sleeve during a dose administration step. Such a piston rod may comprise a piston rod that rotates during the dose administration step. The drive sleeve 224 is not illustrated in FIG. 1 but illustrated in FIG. 2.

The cartridge housing 106 of the drug delivery device 100 has a distal end and a proximal end. Preferably, the distal end of the cartridge housing 106 comprises a hub 108 for attaching a removable needle assembly. However, other needle assembly connection mechanisms could also be used. If the drug delivery device 100 comprises a resettable device, the cartridge proximal end is removably connected to the dose setting mechanism 104. In one preferred embodiment, cartridge housing proximal end is removably connected to the dose setting mechanism 104 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 104 of the drug delivery device illustrated in FIG. 1 may be utilized as a reusable drug delivery device. (i.e., a drug delivery device wherein a dose setting mechanism can be reset). Where the drug delivery device 100 comprises a reusable drug delivery device, the cartridge is removable from the cartridge housing 106. With such a reusable drug delivery device, the cartridge may be removed from the device 100 without destroying the device 100 by merely having the user disconnect the dose setting mechanism 104 from the cartridge housing 106.

In use, once the cap is removed, a user can attach a suitable needle assembly to the hub 108 provided at the distal end of the cartridge housing 106. Such needle assembly may be, for example, screwed onto a distal end of the housing 106 or alternatively may be snapped onto this distal end. After use, the replaceable cap may be used to re-cover the cartridge housing 106. Preferably, the outer dimensions of the replaceable cap are similar or identical to the outer dimensions of the dose setting mechanism 104 so as to provide an impression of a unitary whole when the replaceable cap is in position covering the cartridge housing 106 when the device is not in use.

Figure 2:
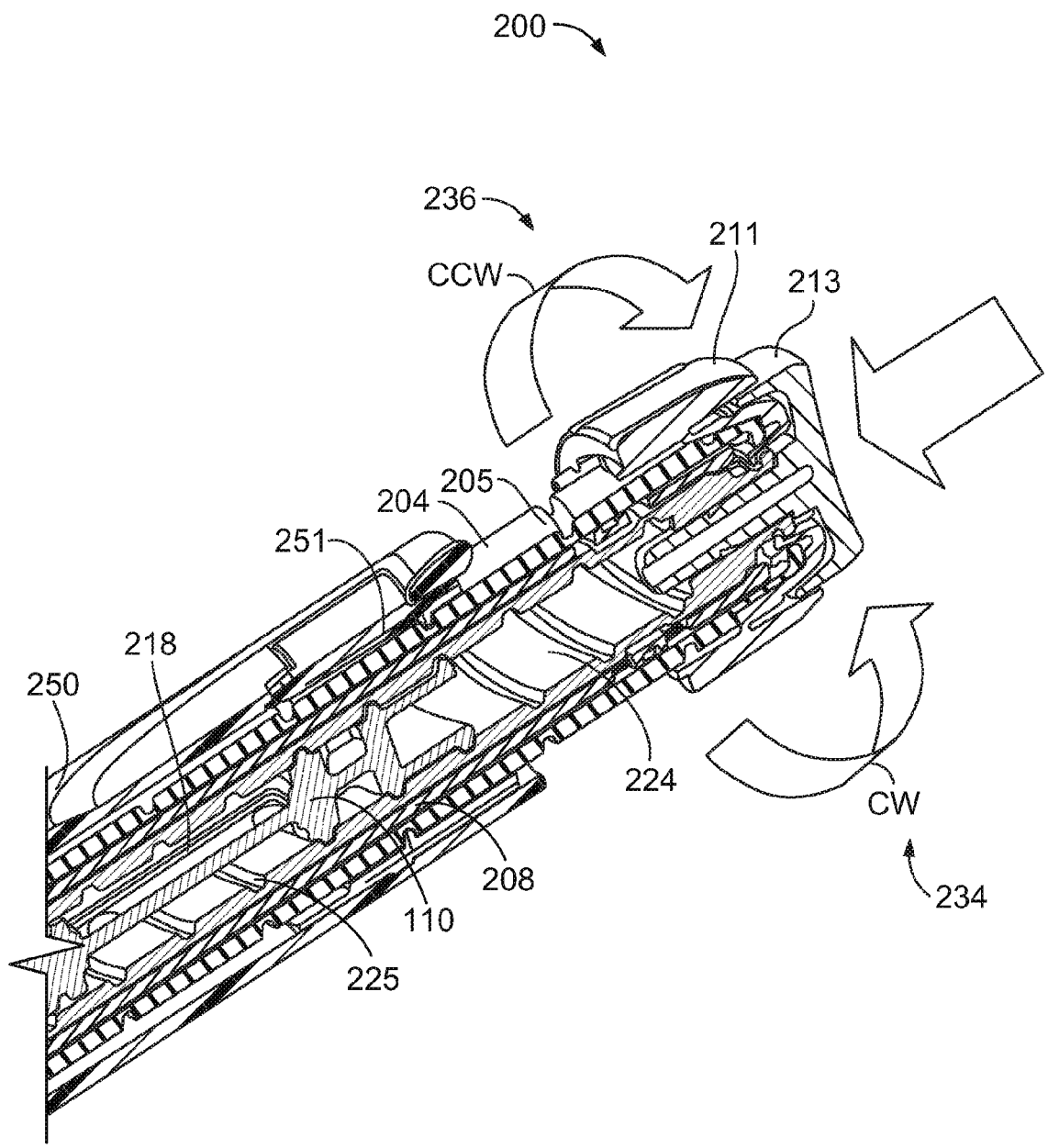
FIG. 2 illustrates a close-up, perspective view of one aspect of the dose setting mechanism illustrated in FIG. 1 during an operation step.

FIG. 2 illustrates a close-up, perspective view of one aspect of a dose setting mechanism 200, similar to the dose setting mechanism 104 illustrated in FIG. 1. As illustrated, the dose setting mechanism 200 comprises a dose setting mechanism housing 250 and this housing comprises a threaded female groove 251 provided along an inner surface of the housing 250. This threaded groove 251 is in threaded engagement with a helical male groove 205 provided along an outer surface of a dose dial component 204. A proximal end of the dose dial component 204 is operably coupled to a rotatable dose dial grip 211 and a dose button 213. A clutch 208 is operably coupled to the dose button 213 and is positioned between the dose dial component 204 and a drive sleeve 224. The clutch 208 disengages the drive sleeve 224 from the dial component 204 allowing relative rotation during dose delivery and rotationally locks the drive sleeve 224 to the dial component 204 during dose setting. This principle of a clutch 208 between the drive sleeve 224 and the dose dial component 204 is similar to the mechanism disclosed in WO 2004/078239 A1. The drive sleeve 224 comprises an internal thread 225 that is in threaded engagement with a piston rod 218, such as a piston rod that can rotate during an injection step.

As illustrated, to set a dose, the dose dial grip 211 may be rotated in a clockwise direction 234. When dialing the dose dial grip 211 in the clock wise direction, as the dose dial grip is coupled to the dose dial component 204 which is in threaded engagement to the internal rib 251 of the housing 250, the dose dial component 204 rotates and translates out of the housing 250 in a proximal direction. As the drive sleeve 224 is operatively coupled to the dose dial component 204 via the clutch 208, the drive sleeve 224 also rotates out of the housing in the proximal direction along with the clutch 208. If an error is made by selecting a dose greater than a desired dose, the dose dial grip 211 is merely rotated in the opposite or counter clock wise direction 236 to reduce this dose. As will be explained in greater detail below, if a dose has been selected greater than a predetermined minimum dose, this selected dose can be administered by pressing on the dose button 213. In addition, in one arrangement, if a dose has been selected smaller than or equal to a priming dose, this priming dose can be administered by pressing on the dose button 213.

Figure 3:
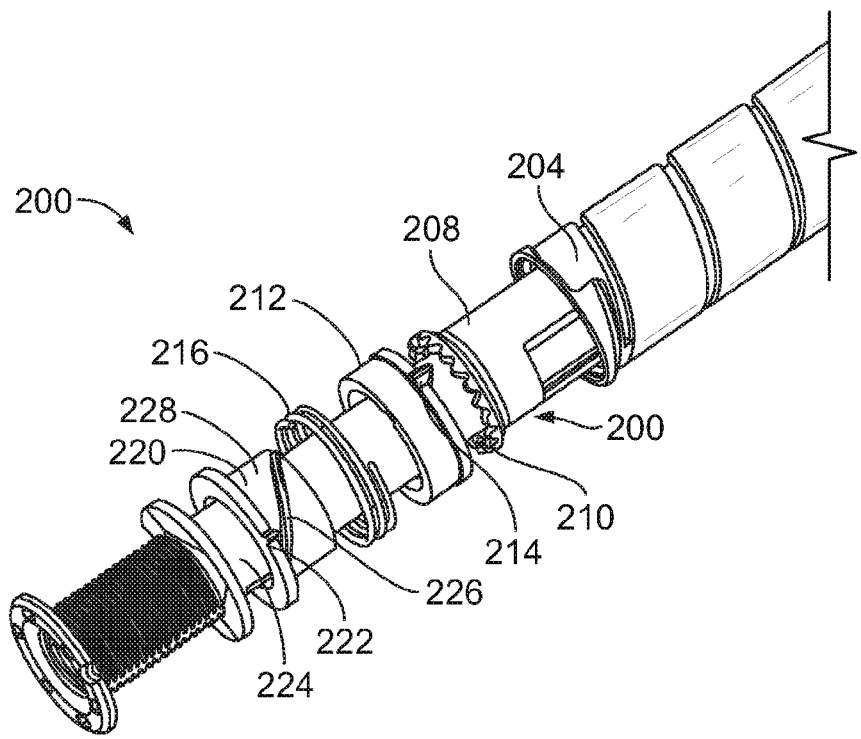
FIG. 3 illustrates an exploded view of a portion of the dose setting mechanism of the pen-type drug delivery device illustrated in FIG. 2.
Figure 4:
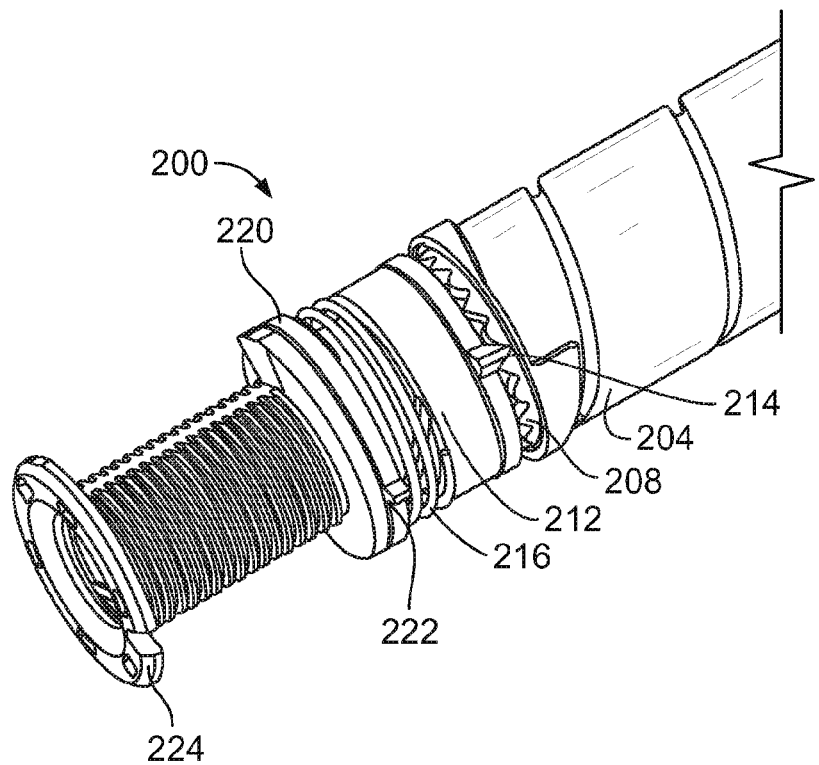
FIG. 4 illustrates a close up view of the dose setting mechanism components illustrated in FIG. 3 in an assembled state.

FIG. 3 illustrates an exploded view of certain internal component parts of a dose setting mechanism 200 illustrated in FIG. 2. FIG. 4 illustrates a close up view of the dose setting mechanism components illustrated in FIG. 3 in an assembled state. As illustrated, the dose setting mechanism 200 comprises a clutch blocker 220, clutch plate 212, and a compression spring 216 situated between the blocker 220 and the plate 212. The clutch blocker 220 is supported on a flange-like protrusion of the drive sleeve 224. The spring 216 is supported on the clutch blocker 220 and the clutch plate 212 such that the spring 216 pushes these two components apart. Further, these component parts 212, 216, 220 are arranged to act on a clutch 208. Also shown in FIG. 3 is the dose dial component 204 and the driver component 224. The dose dial component 204 and driver 224 are positioned within a dose setting mechanism housing, such as the housing 250 illustrated in FIG. 2.

As may be seen from FIGS. 3 and 4, the clutch plate 212 comprises a keying feature in the form of at least one radial key 214. This key is configured to run in an axial spline 258 provided along the inner surface 254 of the housing 250 of the device. The axial spline 258 (shown in FIG. 6) constrains the clutch plate radial key 214 and hence the clutch plate 212 to axial movement during both the dose setting and dose dispensing procedures and prevents rotation of the clutch plate 212.

Figure 6:
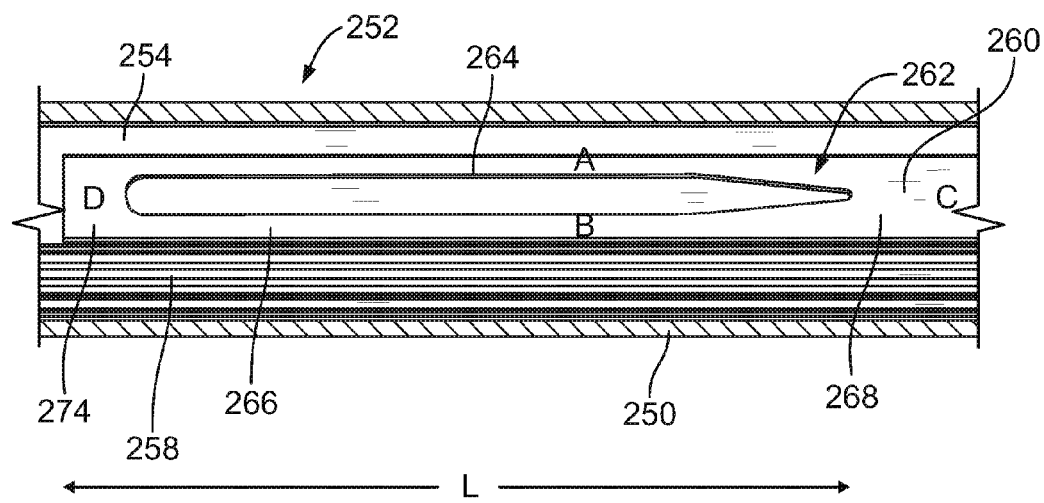
FIG. 6 illustrates a perspective cross sectional view of a portion of the dose setting mechanism housing illustrated in FIG. 5.

In addition, the clutch blocker 220 also comprises a keying feature in the form of at least one radial key 222 and this clutch blocker radial key 222 runs in the dual state path 262 (shown in FIG. 6). In one preferred arrangement, both the clutch blocker 220 and the clutch plate 212 each have two radial keying features that may be separated by 180 degrees. However, the number and angular separation between these radial keying features could be different, for example if a different number of keying features were used.

Figure 5:
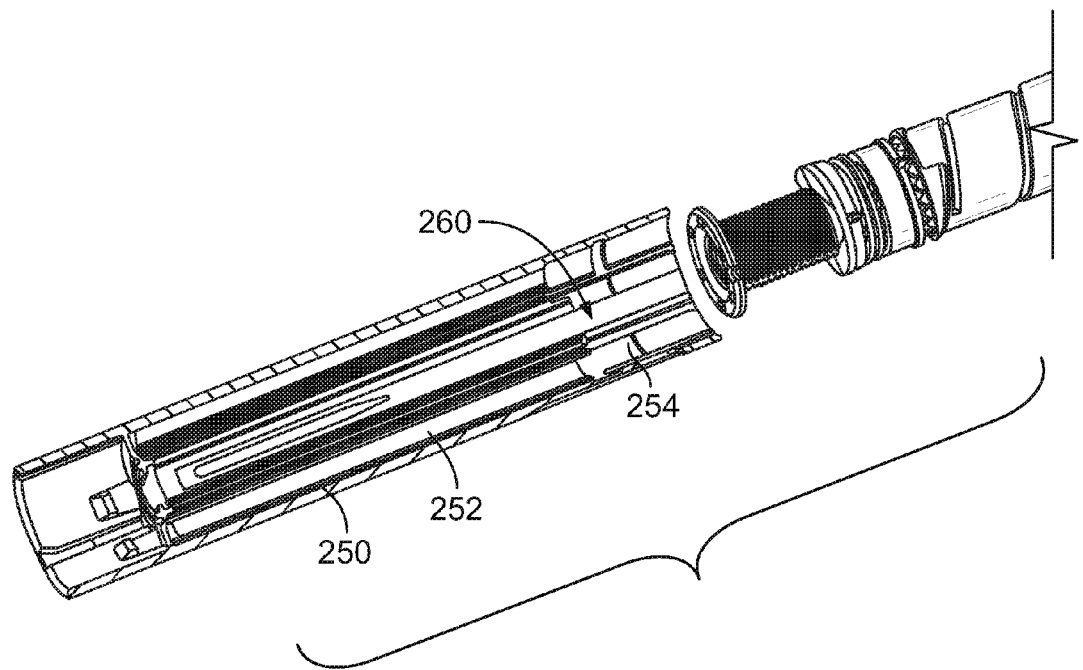
FIG. 5 illustrates a perspective view of the dose setting mechanism illustrated in FIG. 4 along with an accompanying dose setting mechanism housing, such as the dose setting mechanism housing illustrated in FIG. 1.

FIG. 5 illustrates a perspective view of a dose setting mechanism housing 250 configured for use with the dose setting mechanism 200 illustrated in FIGS. 3-4. In addition, FIG. 6 illustrates a close up view of a portion of the housing 250 illustrated in FIG. 5. As illustrated in FIGS. 5 and 6, the housing 250 comprises a track 260 along an internal surface 254 of the housing 250. Preferably, this track 260 comprises a dual state path 262 in which the clutch blocker keying feature 222 (illustrated in FIGS. 3 and 4) is constrained to run. In one preferred arrangement, this dual state path 262 comprises two separate tracks: a first track 264 labelled 'A' and a second track 266 'B.'

In this exemplary illustrated arrangement, both the first track and the second track 264, 266 extend along a first portion 252 of the housing 250 as illustrated in FIG. 5. In FIG. 6, this first portion 252 is illustrated as having a length designated as a length "L". The length of the first portion 252 may extend substantially the entire length of the dose setting housing 250 from its distal end to its proximal end. However, and as will be described in greater detail below, the lengths of these tracks may be varied, either shorter or longer, based on a certain selected predefined minimum dose for a particular drug delivery device and/or a particular medicament to be administered. As those of skill in the art will recognize, different drug delivery devices used for different medicaments, or different therapeutic profiles may have different track configurations and/or track lengths and/or track widths.

In addition, the dual state path 262 further comprises a wider third track 268 labeled in FIG. 6 as 'C' and this third track 268 is generally positioned near a proximal end of the housing 250. This third track 268 allows increased rotation of the clutch blocker radial key feature 222 and hence increased rotation of the clutch blocker 220. Increased rotation of the clutch blocker 220 allows the dose setting mechanism 200 to dispense a selected dose once the selected dose meets or exceeds a predetermined minimum dose. This is because increased rotation of the clutch blocker 220 allows the clutch 208 to disengage the drive sleeve 224 from the dial component 204 allowing relative rotation and therefore dose delivery. In this illustrated arrangement, only one dual state path 262 is illustrated along the inner surface 254 of housing. However, two or more sets of dual state paths may be envisaged to constrain one or more radial key features on the clutch blocker 220.

As may be seen in FIG. 3, the clutch blocker 220 comprises an outer thread 226 provided along an outer surface 228 of the clutch blocker 220. This outer thread 226 provides a means so that the clutch plate 212 and the clutch blocker 220 may be in threaded engagement with each other. In such an arrangement, axial travel of the clutch plate 212 (i.e., when forced downwards by the dose button) will tend to cause the clutch blocker 220 to rotate unless rotation is prevented by its keying feature 222 running in the first path 264 'A' of the dual state path 262.

Preferably, and as may be seen from FIGS. 3-4, a distal end of the clutch 208 comprises a plurality of teeth 210 that engage with a proximal end of the clutch plate 212. Therefore, when the dose dial component 204 is rotated out of the dose setting mechanism 200 during a dose dialing step, these clutch teeth 210 will tend to bounce over the clutch plate keying feature 214. Preferably, this may occur since there is sufficient compliance in the dose setting mechanism 200 to allow this (due to the single path features allowing a small amount of axial displacement).

The dose setting mechanism 200 blocks normal activation (i.e., downward travel) of the clutch 208 until the predetermined minimum dose limit has been reached. For example, FIG. 7 illustrates a cross sectional view of an initial position of the dose setting mechanism 200 illustrated in FIG. 2 before a minimum dose has been selected. As described in detail in WO 2004/078239 A1, normal activation of the device 200 requires the steps of pushing button 213 in the distal direction, which in turn pushes clutch sleeve 208 in the distal direction, thus de-coupling the dose dial component 204 from the drive sleeve 224. Only after this de-coupling step, which allows the dose dial component 204 to be rotated back along the helical path of threads 205, 251 while the clutch sleeve 208 and the drive sleeve 224 rotationally fixed to the clutch sleeve 208 are allowed to move axially in the distal direction guided by spline 258, a set dose can be injected.

In this initial position, the spring 216 between the clutch blocker 220 and the clutch plate 212 is expanded, i.e. the clutch plate 212 is located at the proximal end (upper end in FIG. 7) of the clutch blocker 220. In addition, the clutch sleeve 208 abuts the clutch plate 212 with teeth 210 engaging the clutch plate keying feature 214. Thus, as the clutch blocker 220 and the clutch plate 212 are in threaded engagement via outer thread 226 any axial movement of the clutch plate 212 (induced by a distal movement of the clutch sleeve 208 during activation) relative to the clutch blocker 220 in the distal direction (downwards in FIG. 7) would also require a relative rotational movement between the clutch blocker 220 and the clutch plate 212 along the helical path of the outer thread 226. However, as both, the clutch blocker 220 and the clutch plate 212, are held unrotatably within the housing 250 via splines 264 and 258, respectively, the clutch is prevented from moving in a distal direction by the clutch blocker 220. In this initial position, the dual state path 262 constrains the clutch blocker radial key 222 to move axially without rotation up to a minimum dose limit.

Once this radial key 222 reaches the predefined minimum dose limit, the clutch blocker 220 radial key 222 may rotate if the clutch 208 is actuated upon by the dose button 213 located at the proximal end of the dose setting mechanism 200 (see FIG. 2). Thus, the clutch is allowed to de-couple the dose dial component 204 from the drive sleeve 224.

Blocking downward travel of the clutch 208 prevents the clutch 208 from rotationally disengaging from the dose dial component 204 and causes the device to lock up: the device cannot perform an injection step. As such, the dose dial component 204 cannot rotate back into the housing of the dose setting mechanism 200 during the attempted injection step as it is constrained to axial movement by the clutch 208 due to the clutch blocker 220 preventing clutch 208 disengagement.

This method of blocking the clutch movement in order to prevent dispense of dose below the minimum dose has a number of advantages over alternative methods of locking the dispense mechanism (e.g. methods that rely on introducing additional friction). For example, blocking the clutch movement provides a very well defined "lock" without any risk of slippage or any movement of either dose button 113 or dial component 204. This therefore provides clear feedback to the user that the device is locked.

Operation of the dose setting mechanism is as follows with reference to the respective Figures where noted. For example, during a dose setting step, the keying feature 222 of the clutch blocker 220 runs in the first path 264 'A' of the dual state track 262 (FIG. 6) until the minimum dose limit is reached. At the minimum dose limit the keying feature 222 of the clutch blocker 220 enters the wider section of the third path 268 'C' and dispensing is enabled. As dialing out proceeds yet further, the clutch blocker 220 moves further along the wider section of the third path 268 'C', but (unless the dose button is pressed) the clutch blocker 220 does not rotate due to the action of spring 216 biasing the clutch blocker 220 helically along the outer thread 226. In other words, as the spring 216 pushes the clutch plate 212 to be located at the proximal end (upper end in FIG. 7) of the clutch blocker 220 this also defines the relative rotational position of the clutch plate 212 and the clutch blocker 220 due to the threaded engagement of these two component parts. Thus, spring 216 biases the clutch blocker 220 in a position in which the keying feature 222 of the clutch blocker 220 is guided in the first path 264 'A' of the dual state track 262. As such, the clutch blocker keying feature 222 remains aligned with the first path 264 'A'. Consequently, if the user dials out beyond the minimum dose, but then dials down counter-clockwise (CCW) to less than the minimum dose, the clutch blocker keying feature 222 will re-enter the first path 264 'A.' As such, dispensing of this set dose (i.e., a dose less than the predetermined minimum dose) becomes inhibited once more. In certain applications, this may be an important feature as it prevents the user from bypassing the minimum dose preventing functionality by dialing above the minimum dose and then dialing back down to a lower dose below the minimum.

FIG. 8 illustrates a cross sectional view of a second position of the dose setting mechanism 200 after at least a minimum dose has been selected and the selected dose is being administered. To dispense the set dose, the user presses the dose button of the dose setting mechanism 200 and so acts to move the clutch plate 212 downwards (in a distal direction) and this compresses the spring 216. Due to the threaded engagement of the clutch blocker and the clutch plate, this causes the clutch blocker 220 to rotate. As can be seen by comparing the position of the clutch blocker 220 in FIG. 7 and its position in FIG. 8, the blocker has been rotated so that its radial key(s) 222a and 222b illustrated in FIG. 7 (as mentioned above, embodiments with only one single radial key 222 or even more keys are suitable, too) are no longer visible in FIG. 8 (since it has rotated). Rotation of the clutch blocker 220 is permitted only if the clutch blocker keying feature 222 has passed beyond the narrow section of the first path 264 'A' and entered the wider section of the third path 268 'C'.

If rotation is permitted, the clutch blocker 220 moves from its alignment with the first path 264 'A' and instead moves into alignment with the second path 266 'B' when the dose button 113 is pressed. So as the medicament is dispensed down below the minimum dose limit, the keying feature 222 of the clutch blocker 220 enters the second path 266 'B', and retains the device in the dispensing condition until the dose button has been pressed in fully and all of the dialed quantity has been dispensed.

If rotation of the clutch blocker 220 is not permitted (i.e., when the clutch blocker keying feature 222 remains within the first path 264 'A'), then the outer thread 226 in threaded engagement with the clutch plate 212 prevents the clutch plate 212 and thereby also the clutch from moving towards the clutch blocker 220 and therefore prevents the clutch 208 from moving distally with respect to the dose dial component and thereby prevents the clutch 208 from releasing the dose dial component 204. As such, the clutch 208 is effectively blocked from moving axially and dispensing is not possible.

At the completion of dose dispense step, the clutch blocker 220 resets itself automatically into the blocked condition when, at the end of dose delivery, the user removes his/her finger from the dose button. As mentioned previously, during dispense, the clutch blocker 220 moves along the second path 266 'B.' At the end of dispense, the second path 266 B' widens out and links with yet a fourth path 274 that is labelled D in FIG. 5. When this fourth path 274 'D' is reached, the compression spring 216 will return the clutch blocker back to the first path 264 'A' when the user removes his/her finger from the dose button. This resets the dose setting mechanism to its original condition where it is now ready to dial out the next dose. The spring 216 performs this function because it is under compression and acts to rotate the clutch blocker 220 relative to the clutch plate 212 and the housing 250 through the helical linkage to the original state as shown in FIG. 7.

An added benefit of this design is that by altering the length 'L' of the dual state path 262 the minimum dose threshold may also be altered. This design feature, in conjunction with a maximum dose limit, means that a range of therapeutically effective dose windows may be created thus tailoring the dose regime to meet the needs of a particular patient requirements or a specific therapy.

Furthermore, by altering the length of path 'D' of the dual state path a second permissible dose window is permitted. This second dose window starts at 0 units dialed and ends at the point where path 'D' divides into the first path 'A' and the second path 'B'. The second dose window can therefore be designed to enable the user to dispense "air shots" or "priming doses" that would otherwise be below the minimum dose threshold.

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

As disclosed herein, the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

TABLE 1

| Dialled Insulin Dose | Pen Number | | | |
|---|---|---|---|---|
| | 1 | 2 | 3 | 4 |
| 2 | | | | |
| 4 | | | | |
| 6 | | | | |
| 8 | | | | |
| 10 | | | | |
| 12 | | | | |
| 14 | | | | |
| 16 | | | | |
| 18 | | | | |
| 20 | | | | |
| 22 | | | | |
| 24 | | | | |
| 26 | | | | |

TABLE 1-continued

| 28 | | | | |
|---|---|---|---|---|
| 30 | | | | |
| 32 | | | | |
| 34 | | | | |
| 36 | | | | |
| 38 | | | | |
| 40 | | | | |
| 42 | | | | |
| 44 | | | | |
| 46 | | | | |
| 48 | | | | |
| 50 | | | | |
| 52 | | | | |
| 54 | | | | |
| 56 | | | | |
| 58 | | | | |
| 60 | | | | |
| 62 | | | | |
| 64 | | | | |
| 66 | | | | |
| 68 | | | | |
| 70 | | | | |
| 72 | | | | |
| 74 | | | | |
| 76 | | | | |
| 78 | | | | |
| 80 | | | | |

| Legend |
|---|
| Dose may be dialled and delivered |
| Low dose - Cannot be dispensed |
| High dose - Cannot be dialled |

TABLE 2

| Dialled Insulin Dose | Pen Number | | | |
|---|---|---|---|---|
| | 1 | 2 | 3 | 4 |
| 2 | | | | |
| 4 | | | | |
| 6 | | | | |
| 8 | | | | |
| 10 | | | | |
| 12 | | | | |
| 14 | | | | |
| 16 | | | | |
| 18 | | | | |
| 20 | | | | |
| 22 | | | | |
| 24 | | | | |
| 26 | | | | |

TABLE 2-continued

| | | | | |
|---|---|---|---|---|
| 28 | | | | |
| 30 | | | | |
| 32 | | | | |
| 34 | | | | |
| 36 | | | | |
| 38 | | | | |
| 40 | | | | |
| 42 | | | | |
| 44 | | | | |
| 46 | | | | |
| 48 | | | | |
| 50 | | | | |
| 52 | | | | |
| 54 | | | | |
| 56 | | | | |
| 58 | | | | |
| 60 | | | | |
| 62 | | | | |
| 64 | | | | |
| 66 | | | | |
| 68 | | | | |
| 70 | | | | |
| 72 | | | | |
| 74 | | | | |
| 76 | | | | |
| 78 | | | | |
| 80 | | | | |

Dose may be dialled and delivered
Low dose - Cannot be dispensed
High dose - Cannot be dialled

TABLE 3

| Dialled Long Acting Insulin Dose | Premix Pen Number | | | | | |
|---|---|---|---|---|---|---|
| | 1 | 2 | 3 | 4 | 5 | 6 |
| | Mix ratio (insulin: GLP-1) | | | | | |
| | 0.83 | 0.665 | 0.53 | 0.43 | 0.35 | 0.285 |
| 2 | | | | | | |
| 4 | | | | | | |
| 6 | | | | | | |
| 8 | | | | | | |
| 10 | | | | | | |
| 12 | | | | | | |
| 14 | | | | | | |
| 16 | | | | | | |
| 18 | | | | | | |
| 20 | | | | | | |
| 22 | 18.3 | | | | | |
| 24 | 19.9 | | | | | |
| 26 | 21.6 | | | | | |

TABLE 3-continued

| Dialled Long Acting Insulin Dose | 1 | 2 | 3 | 4 | 5 | 6 |
|---|---|---|---|---|---|---|
| 28 | | 18.6 | | | | |
| 30 | | 20.0 | | | | |
| 32 | | 21.3 | | | | |
| 34 | | | 18.0 | | | |
| 36 | | | 19.1 | | | |
| 38 | | | 20.1 | | | |
| 40 | | | 21.2 | | | |
| 42 | | | | 18.1 | | |
| 44 | | | | 18.9 | | |
| 46 | | | | 19.8 | | |
| 48 | | | | 20.6 | | |
| 50 | | | | 21.5 | | |
| 52 | | | | | 18.2 | |
| 54 | | | | | 18.9 | |
| 56 | | | | | 19.6 | |
| 58 | | | | | 20.3 | |
| 60 | | | | | 21.0 | |
| 62 | | | | | 21.7 | |
| 64 | | | | | | 18.2 |
| 66 | | | | | | 18.8 |
| 68 | | | | | | 19.4 |
| 70 | | | | | | 20.0 |
| 72 | | | | | | 20.5 |
| 74 | | | | | | 21.1 |
| 76 | | | | | | 21.7 |
| 78 | | | | | | |
| 80 | | | | | | |

GLP-1 Dose - may be dialled and delivered
Low dose - Cannot be dispensed
High dose - Cannot be dialled

The invention claimed is:

1. Dose setting mechanism for a drug delivery device, the mechanism comprising:
   a drug delivery device housing;
   a dose dial component positioned at least partly in the housing and rotatable during dose setting and dose delivery,
   characterized by
   at least one dual state track within the housing that is axially and rotationally fixed with respect to the housing, which comprises a first track, a second track, and a third track;
   a clutch plate rotationally fixed relative to the housing; and
   a clutch blocker in threaded engagement with the clutch plate and having at least one radial key engaged with the at least one dual state track,
   wherein the radial key is engaged with the first track during dose setting until a predetermined minimum dose is dialed with the dose dial component and with the second track after a predetermined minimum dose is dialed with the dose dial component.

2. Mechanism according to claim 1 further comprising a biasing member positioned between the clutch blocker and clutch plate.

3. Mechanism according to claim 1 wherein the clutch blocker comprises a distal end and the clutch plate comprises a proximal end, wherein the distal end of the clutch blocker is separated from the proximal end of the clutch plate by a given distance during dose setting and by a distance less than the given distance during dose delivery.

4. Mechanism according to claim 1 wherein the clutch plate has at least one radial key splined to the housing to prevent rotation during dose setting and dose delivery.

5. Mechanism according to claim 1 wherein the clutch blocker and clutch plate are configured to prevent delivery of a dose when a set dose is less than a minimum predetermined dose.

6. Mechanism according to claim 5 wherein the clutch blocker and clutch plate are configured to prevent delivery of the dose when the set dose is less than the minimum predetermined dose but allows the delivery of the set dose if the set dose is less than a predetermined maximum priming dose.

7. Mechanism according to claim 1 wherein the dual state track has an axial length that is proportional to a predetermined minimum dose.

8. Mechanism according to claim 1 further comprising a fourth track wherein the clutch blocker key is engaged with the fourth track when a dose of zero to a predetermined maximum priming dose is dialed.

9. Mechanism according to claim 1 wherein the dual state track, the clutch plate and the clutch blocker are configured to prevent a relative axial and/or a relative rotational movement between the clutch plate and the clutch blocker when a set dose is less than a minimum predetermined dose.

10. Mechanism according to claim 1 wherein the clutch plate is a sleeve-like or ring-like component comprising means for rotationally coupling the clutch plate to a clutch member.

11. Mechanism according to claim 1 wherein the clutch blocker is a sleeve-like component which is at least partly surrounded by the clutch plate.

12. Mechanism according to claim 1 further comprising a drive sleeve being rotatable during dose setting and axially displaceable during dose delivery.

13. Mechanism according to claim 12 wherein the drive sleeve is rotationally locked to a clutch member and wherein the drive sleeve comprises means supporting the clutch blocker in the distal direction.

14. A method of setting at least a predetermined minimum dose of a medicament comprising the steps of providing a drug delivery device housing;

axially and rotationally fixing a dual state track within the housing with respect to the housing, wherein the dual state track comprises a first track, a second track, and a third track;

positioning a dose dial component at least partly in the housing, the dose dial component being rotatable during dose setting and dose delivery, providing a clutch member that is rotatable during dose setting and non-rotatable during dose delivery;

rotationally fixing a clutch plate relative to the housing;

engaging a clutch blocker with the clutch plate by way of a thread; and engaging a radial key of the clutch blocker with the dual state track wherein the radial key runs in the first track until a predetermined minimum dose has been dialed.

* * * * *